(12) United States Patent
Gareis et al.

(10) Patent No.: US 6,309,845 B1
(45) Date of Patent: Oct. 30, 2001

(54) METHOD OF ESTABLISHING THE ORIGIN OF USEFUL ANIMALS AND PRODUCTS PRODUCED THEREFROM

(76) Inventors: Manfred Gareis, Stegersgasse 21, 95349 Thurnau; Martin Groschup, Schickhardtstrasse 4, 72072 Tübingen, both of (DE)

( * ) Notice: Subject to any disclaimer, the term of this patent is extended or adjusted under 35 U.S.C. 154(b) by 0 days.

(21) Appl. No.: 09/297,001

(22) PCT Filed: Oct. 22, 1997

(86) PCT No.: PCT/DE97/02439

§ 371 Date: Jun. 7, 1999

§ 102(e) Date: Jun. 7, 1999

(87) PCT Pub. No.: WO98/18003

PCT Pub. Date: Apr. 30, 1998

(30) Foreign Application Priority Data

Oct. 23, 1996 (DE) .............................. 196 43 682

(51) Int. Cl.[7] .......... G01N 33/53; G01N 33/12; G09F 3/00; A61B 10/00; A23L 1/313
(52) U.S. Cl. .......... 435/7.1; 40/300; 424/9.81; 426/652; 436/21
(58) Field of Search .............. 40/300; 119/655; 395/800.26; D30/155; 435/7.92, 7.1, 326; 530/403; 427/2.14, 278.1; 424/96, 9.81, 422; 436/510, 513, 20, 823, 21; 426/652

(56) References Cited

U.S. PATENT DOCUMENTS 3,788,296 * 1/1974 Klatt et al. .............................. 128/268
4,152,412 5/1979 Brewer .
4,909,250 * 3/1990 Smith .................................... 606/117
5,077,194 * 12/1991 Heeny et al. .............................. 435/5

FOREIGN PATENT DOCUMENTS 0 336 800 10/1989 (EP) .
2 271 848 A 4/1994 (GB) .

OTHER PUBLICATIONS

Black, J.G. 1996. Microbiology Principles and Applications, third edition. Prentice–Hall, Inc., p. 494.*
Douch et al. 1996. Phenotypic markers for selection of nematode resistant sheep. International journal for parasitology. vol. 26, No. 8/9, pp. 899–911.*
Chowdhuri Sep. 1996. Construction and characterization of an attenuated bovine herpesvirus type 1 (BHV–1) recombinant virus. Veterinary Microbiology. vol. 52, pp. 13–23.*
XP–002059374, 1/1—(C) WPI / Derwent.
Patent Abstracts of Japan, Publication No. 09229932, Publication Date May 9, 1997.
XP–002059373, 12/18—(C) File Agricola.
WO 95/06723.

* cited by examiner

*Primary Examiner*—Laurie Scheiner
*Assistant Examiner*—Shanon A. Foley
(74) *Attorney, Agent, or Firm*—Pearne & Gordon LLP

(57) ABSTRACT

The invention concerns a method of establishing the origin of useful animals, in particular cattle, pigs and the like. This method comprises the following steps: a) the live animal is marked biologically by applying at least one antigen which is harmless to the animal and humans: and b) the specific antibodies formed by the application of the at least one antigen are identified by means of an enzymimmunological or immunochemical detection process.

31 Claims, No Drawings

METHOD OF ESTABLISHING THE ORIGIN OF USEFUL ANIMALS AND PRODUCTS PRODUCED THEREFROM

This application is a 371 of PCT/DE97/02439 Oct. 22, 1997.

The invention relates to a method and a use for identifying the origin of useful animals, in particular of cattle, pigs and the like, and of products derived therefrom.

The prior art describes providing useful animals such as cattle and pigs with an identification which identifies the origin, and this identification is borne as an imprint on a tag attached to the ear of the useful animal (tattooing, transponders and other systems). Prior to slaughtering, the useful animals are combined in groups, depending on their origin. The carcasses are then provided with a group-specific stamp. In recent years, it has become an established practice to additionally provide accompanying documents with each useful animal so as to increase the reliability of the identification of origin.

However, the prior-art identifications of origin are disadvantageous in many ways. For example, it is common practice that import restrictions or bans are circumvented by exchanging or forging the tags and also forging the corresponding accompanying documents. The making out of accompanying documents involves a great deal of bureaucracy.

The prior-art identification of origin is insufficient in particular for the reliable containing of illegal trading, for example in beef which may be contaminated with BSE pathogen or its use for making meat products such as dog food and the like.

The object of the invention is to overcome the disadvantages of the prior art. In particular, it is intended to provide a forgery-proof identification with which not only the origin of the live useful animal, but also products derived therefrom, such as meat, meat products and foodstuffs of animal origin, can be identified in a reliable fashion.

This object is achieved by the features of claims 1 and 14. Advantageous embodiments can be seen from the features of claims 2 to 13 and 15 to 23.

To achieve the object, a method is provided which comprises the following steps:
a) biological tagging of the live useful animal by applying at least one immunogen which is harmless to the useful animal and humans, and
b) detection, in the live useful animal or in products derived therefrom of the specific antibodies formed by applying at least one immunogen, using an enzyme-immunological or immunochemical detection method.

The advantage of the method according to the invention is that the biological tag cannot be separated from the useful animal and therefore not exchanged or forged. Moreover, it is possible to identify the origin of meat without stamp of origin, even of meat used for making meat products.

The immunogen(s) used is/are preferably a protein and/or peptide which, in normal livestock management, reaches the organism of the useful animal neither as vaccine nor via the food chain nor via the environment, and against which no antibodies are formed naturally in the useful animals. A protein and/or peptide coupled to a matrix is expediently used.—This simple procedure results in a specific tag which is readily detectable and fully acceptable for human consumption.

According to one embodiment, the immunogen is such that the specific antibodies formed remain permanently in the organism of the useful animal and can be detected by means of an enzyme-immunological or immunochemical detection method.—In this manner, tagging can be effected in a single application, expediently immediately after the useful animal has been born. Application can be effected by applying the immunogen to the useful animal by means of an injection. Also, the immunogen may also be applied via the mucous membrane, preferably the nasal mucosa, of the useful animal, for example using a nasal spray, or by means of an implant.

It is advantageous to apply a mixture of several different immunogens. A first immunogen can be used for identifying the region of origin, such as Western Europe, Eastern Europe, South America and the like, a second immunogen for identifying the country of origin, and a third immunogen for identifying administrative units of the country in question. Individual production and distribution organizations (for example producer groups, quality meat programs) may use biological tagging of the livestock or products derived therefrom, either as an alternative or by way of supplementation. Materials on which the antibodies can be detected are, in the case of the live useful animal, the blood, the milk or other body secretions, and in the case of the slaughtered animal also blood and body secretions, such as meat juices released naturally or by expressing.

To identify the antibodies, it is preferred to use one or more of the following detection methods as enzyme-immunological or immunochemical detection method: enzyme-linked immunosorbent assay (=ELISA), enzyme immunoassay (=EIA) and radioimmunoassay (=RIA). The enzyme-immunological or immunochemical detection is particularly simple if it is carried out using test sticks.—If the tagging operation is restricted to official veterinarians, the origin of products obtained from, for example, slaughtered useful animals can be checked and established by virtually anybody.

The invention also provides the use of at least one
a) immunogen which is harmless to useful animals and humans, for the biological tagging of the live useful animal and of products derived therefrom, and of
b) an enzyme-immunological or immunochemical detection method for detecting, in the live useful animal or in products derived therefrom, the specific antibodies formed by applying the at least one immunogen.

The immunogen can be a protein and/or peptide or a mixture of these which, in normal livestock management, reaches the organism of the useful animal neither as vaccine nor as medicament nor via the food chain and against which no antibodies are formed naturally in the useful animals; the protein and/or peptide may be coupled to a matrix.—The use of an immunogen which is foreign, but harmless, to the organism to be tagged, for biological tagging, allows a surprisingly simple, inexpensive and forgeproof identification of origin.

EXAMPLES

The proteins which stimulate outstanding specific antibody production and which can be applied to the useful animal are immunogens such as keyhole limpet hemocyanine, Aequoria victoria green fluorescent protein, inactive snake toxins and viral proteins. In addition, naturally occurring peptides or polypeptides such as hirudin, pheromonotropin or ranalexin may also be applied. Moreover, synthetic fragments of amino acid subsequences of naturally occurring immunogens may also be used for biotagging. Finally, immunogens which can also be used are artificial proteins and peptides whose amino acid sequence does not correspond to any substance known to date but which are combined or prepared exclusively for biotagging purposes.

Detection of the antigens formed by the abovementioned materials is by customary detection methods such as ELISA, EIA and RIA, preferably using test sticks which are dipped into, for example, the meat juice released naturally by the slaughtered useful animal.

What is claimed is:

1. Method of identifying animals and animal products originating from a specific geographical region, individual production organization, producer group, distribution organization, or quality meat program, comprising the following steps:
   a) biologically tagging a live animal originating from a specific geographical region, individual production organization, producer group, distribution organization, or quality meat program by applying at least one immunogen which is nontoxic to the animal and humans, the immunogen(s) used being at least one protein and/or peptide which, in customary livestock management, reaches the organism of the animal neither as vaccine(s) nor as medicament nor via the food chain nor via the environment and against which no antibodies are formed naturally in the animals,
   b) detecting, in the live animal or in products derived therefrom, the specific antibodies formed by applying the at least one immunogen, using an enzyme-immunological or immunochemical detection method, wherein detection of the specific antibodies indicates the origin of the animal or animal product.

2. Method according to claim 1, wherein said live animal is an animal selected from the group consisting of cattle and pigs.

3. A method according to claim 1, wherein said origin of the animal is a geographical origin of the animal.

4. A method according to claim 1, wherein said origin of the animal is a producer group of the animal.

5. A method according to claim 1, wherein said origin of the animal is a quality meat program of the animal.

6. A method according to claim 1, wherein said origin of the animal is an individual production organization of the animal.

7. Method according to any of the preceding claims, the immunogen being such that the specific antibodies formed remain permanently in the organism of the animal and can be detected by means of enzyme-immunological or immunochemical detection methods.

8. Method according to claim 1, wherein a mixture of several different immunogens is applied.

9. Method according to claim 1 in which a protein and/or peptide coupled to a matrix is/are used.

10. Method according claim 1, wherein the immunogen is applied to the animal by means of an injection.

11. Method according claim 1, wherein the immunogen is applied by means of an implant.

12. Method according to claim 1, wherein the immunogen is applied via the mucous membrane of the animal.

13. Method according to claim 1, wherein meat juices of the slaughtered animal which are released naturally or by expressing are used for detecting the specific antibodies.

14. Method according to claim 1, wherein milk or other body secretions are used for detecting the specific antibodies.

15. Method according to claim 1, wherein blood of the useful animal is used for detecting the specific antibodies.

16. Method according to claim 1, wherein one or more of the following detection methods is/are used as enzyme-immunological or immunochemical detection method; enzyme-linked immunosorbent assay (=ELISA), enzyme immunoassay (=EIA) and radioimmunoassay (=RIA).

17. Method according to claim 1, wherein the enzyme-immunological or immunochemical detection is performed using test sticks.

18. Use of at least one
   a) immunogen which is nontoxic to animals and humans, for the biological tagging of a live animal and of products derived therefrom, said animal originating from a specific geographical region, individual production organization, producer group, distribution organization, or quality meat program, and said immunogen being selected to correlate to the origin of said animal, and of
   b) enzyme-immunological or immunochemical detection method for detecting, in the live animal or in products derived therefrom, the specific antibodies formed by applying the at least one immunogen, and determining said origin of the animal, wherein the immunogen is a protein and/or peptide which, in normal livestock management, reaches the organism of the animal neither as vaccine nor as medicament nor via the food chain and against which no antibodies are formed naturally in the animals.

19. Use according to claim 18, wherein the antigen is such that the specific antibodies formed remain permanently in the organism of the animal and can be detected by means of enzyme-immunological or immunochemical detection methods.

20. Use according to claim 19, wherein the protein and/or peptide is coupled to a matrix.

21. Use according to any of claims 18, 19 and 20, wherein a mixture of several different immunogens is used.

22. Use according to claim 18, wherein meat juices of the slaughtered useful animal which are released naturally or by expressing are used for detecting the antibodies.

23. Use according to claim 18, wherein blood of the animal is used for detecting the specific antibodies.

24. Use according to claim 18, wherein milk of the animal or other body secretions is used for detecting the specific antibodies.

25. Use according to claim 18, wherein one or more of the following detection methods is/are used as enzyme-immunological or immunochemical detection method: enzyme-linked immunosorbent assay (=ELISA), enzyme immunoassay (=EIA) and radioimmunoassay (=RIA).

26. Use according to claim 18, wherein test sticks are used for enzyme-immunological or immunochemical detection.

27. A method of identifying an origin of an animal and of products derived therefrom, said animal having been biologically tagged according to said origin when said animal was alive by applying at least one immunogen which is nontoxic to the animal and humans, said immunogen being a protein and/or peptide which, in customary livestock management, reaches the organism of the animal neither as vaccine nor as medicament nor via the food chain and against which no antibodies are formed naturally in the animal, said method comprising the steps of:
   a) detecting, in the live animal or in products derived therefrom, the specific antibodies formed by the applying of the at least one immunogen selected to indicate the origin of the animal, using an enzyme-immunological or immunochemical detection method, and b) determining said origin of the animal, said origin being selected from the group consisting of a geographical origin of the animal, an individual production organization of the animal, a distribution organization of the animal, and a quality meat program of the animal.

28. A method according to claim 27, wherein said origin of the animal is a geographical origin of the animal.

29. A method according to claim 27, wherein said origin of the animal is a producer group of the animal.

30. A method according to claim 27, wherein said origin of the animal is a quality meat program of the animal.

31. A method according to claim 27, wherein said origin of the animal is an individual production organization of the animal.

* * * * *

UNITED STATES PATENT AND TRADEMARK OFFICE
CERTIFICATE OF CORRECTION

PATENT NO. : 6,309,845 B1  Page 1 of 1
DATED : October 30, 2001
INVENTOR(S) : Manfred Gareis et al.

It is certified that error appears in the above-identified patent and that said Letters Patent is hereby corrected as shown below:

Column 3,
Line 6, delete "useful".

Column 4,
Line 40, delete "useful".

Signed and Sealed this

Fifth Day of November, 2002

Attest:

Attesting Officer

JAMES E. ROGAN
Director of the United States Patent and Trademark Office